United States Patent
Gross

(10) Patent No.: US 9,119,608 B2
(45) Date of Patent: Sep. 1, 2015

(54) ADAPTER FOR OVERPRESSURE PROTECTION, CRYOPROBE HAVING SUCH AN ADAPTER AND CRYOSURGICAL DEVICE WITH OVERPRESSURE PROTECTION

(75) Inventor: Stefan Gross, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 896 days.

(21) Appl. No.: 13/264,504

(22) PCT Filed: Mar. 30, 2010

(86) PCT No.: PCT/EP2010/002017
§ 371 (c)(1),
(2), (4) Date: Nov. 17, 2011

(87) PCT Pub. No.: WO2010/118824
PCT Pub. Date: Oct. 21, 2010

(65) Prior Publication Data
US 2012/0071869 A1  Mar. 22, 2012

(30) Foreign Application Priority Data

Apr. 14, 2009 (DE) .......................... 10 2009 017 370

(51) Int. Cl.
*A61B 18/18* (2006.01)
*A61B 18/02* (2006.01)

(52) U.S. Cl.
CPC ............. *A61B 18/02* (2013.01); *A61B 18/0218* (2013.01); *A61B 2018/0262* (2013.01)

(58) Field of Classification Search
USPC ...................................................... 606/21–22
See application file for complete search history.

(56) References Cited

U.S. PATENT DOCUMENTS

| | | |
|---|---|---|
| 3,913,581 A | 10/1975 | Ritson et al. |
| 5,891,188 A | 4/1999 | Maytal |
| 6,251,105 B1 | 6/2001 | Mikus et al. |
| 2007/0093710 A1 | 4/2007 | Maschke |
| 2008/0114344 A1 | 5/2008 | Xiao et al. |
| 2008/0255552 A1 | 10/2008 | DeLonzor |

FOREIGN PATENT DOCUMENTS

| | | |
|---|---|---|
| CN | 101330880 A | 12/2008 |
| DE | 90 02 065 | 4/1990 |
| DE | 10 2006 003 571 A1 | 8/2007 |

(Continued)

*Primary Examiner* — Nicole F Lavert
(74) *Attorney, Agent, or Firm* — Dickstein Shapiro LLP

(57) ABSTRACT

As disclosed herein, cryoprobes comprising no return line can be operated efficiently and safely on known supply systems for cryoprobes. Typically the supply systems provide a fluid for connected cryoprobes so that they will provide the desired cooling capacity. The cooling capacity can be adjusted through the supply system. An adapter for connecting a supply system with a cryoprobe for open fluid cooling, wherein the adapter comprises: a first fluid adapter connector for connecting a first supply terminal of the supply system; a second fluid adapter connector for connecting a second supply terminal of the supply system; a feed line output for connecting a feed line of the cryoprobe; a first fluid line for the fluid connection of the first fluid adapter connector with the feed line output; and a second fluid line for the fluid connection of the feed line output with the second fluid adapter connector, wherein the fluid flow in the second fluid line is reduced compared the one in the first fluid line.

14 Claims, 2 Drawing Sheets

(56) References Cited

FOREIGN PATENT DOCUMENTS

| DE | 10 2008 038 310 A1 | 12/2009 |
| GB | 2 005 000 A | 4/1979 |
| WO | WO 98/32383 A1 | 7/1998 |
| WO | WO 00/35362 A2 | 6/2000 |
| WO | WO 2004/082749 A2 | 9/2004 |
| WO | WO 2004082749 * | 9/2004 ........... A61B 8/0833 |
| WO | WO 2005/038357 A2 | 4/2005 |
| WO | WO 2009/022335 A1 | 2/2009 |

* cited by examiner

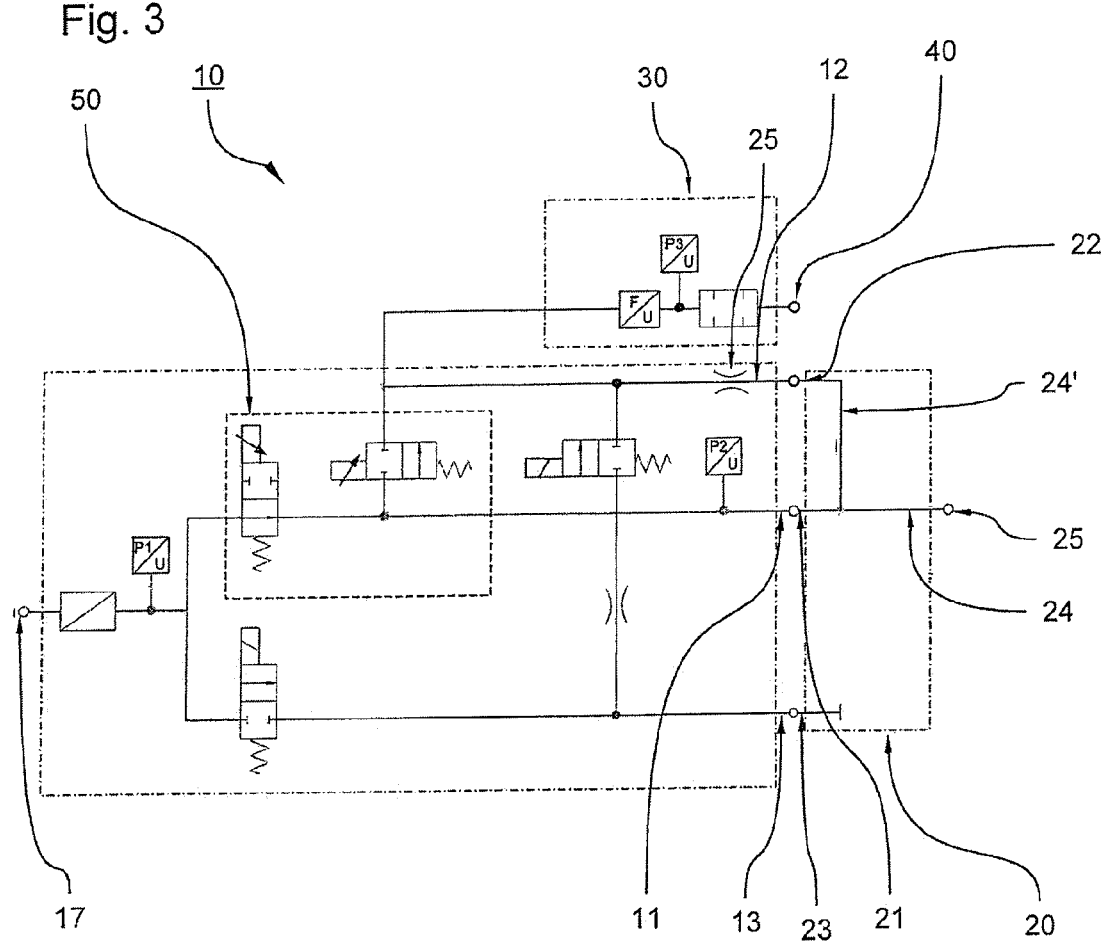

ADAPTER FOR OVERPRESSURE PROTECTION, CRYOPROBE HAVING SUCH AN ADAPTER AND CRYOSURGICAL DEVICE WITH OVERPRESSURE PROTECTION

FIELD OF THE INVENTION

Embodiments of the invention relate to an adapter for connecting a supply system with a cryoprobe, a cryoprobe having such an adapter and a cryosurgical device.

BACKGROUND

Cryotherapy has numerous applications. For example, cryoprobes are used for the destruction of diseased tissue, the taking of tissue samples and/or for the removal of foreign objects. Furthermore, the applied cold can be used to stop hemorrhaging or prevent disadvantageous tissue changes.

In cryotherapy, in particular in cryosurgery, cold is frequently applied by means of a probe in order to achieve a healing effect.

Various methods exist for cooling the instrument, i.e., the cryoprobe. Frequently, the Joule-Thomson effect is utilized. In this case, a fluid, in particular a gas, is expanded near the application site via a nozzle in an expansion chamber, where the fluid experiences a temperature change. Among other things, the cooling capacity is a function of the temperature difference existing at the site of expansion. In order to ensure an effective cooling of the instrument it is necessary to discharge the expanded gas from the expansion chamber without causing any unwanted back-pressure.

In practice, there is a difference between cryoprobes with front pressure regulation and rear pressure regulation. Usually, a cryoprobe comprises a feed line and a return line. The feed line is always configured to be pressure-stable, but there are cryoprobes having a return line that are not pressure-stable. Front pressure regulation is used for adjusting the cooling capacity of such cryoprobes. In this case, the pressure is adjusted in the supply, depending on the desired cooling capacity. The return line has an essentially atmospheric pressure. In rear pressure regulation, the cooling capacity is regulated by the pressure in the return line at constant pressure in the fed line.

Considering probes comprising return lines that are not pressure-stable (front pressure regulation), there is a difference between open (open fluid cooling) and closed systems. In open systems, the fluid is discharged—due to expansion—either indirectly or directly to the environment. A return inside the instrument does not occur or occurs only conditionally. Some of the fluid is discharged into the organ or taken in by the endoscope. However, in conjunction with this, it must be taken into consideration that—for the safety of personnel—it must be ensured that only minimal amounts of fluid escape into the operating room while an operation is being performed.

A supply system for cryoprobes with a feed line and a return line, to which cryoprobes with front pressure regulation as well cryoprobes with rear pressure regulation can be connected, has been known from German publication DE 10 2006 003 571 A1. It is desirable that cryoprobes with open systems also can be connected to such a supply system.

Furthermore, it is an extreme problem that, considering such open systems, there is no possibility of detecting occlusions in the feed line, a functional failure of the pressure adjustment device or any excess pressure building in the systems. In such cases, this can result in damage to the instrument or also danger to the patient or user. Consequently, it is desirable that an overpressure protection or an overpressure safety feature be provided even for open cryoprobes or cryoprobes disposed for open fluid cooling.

SUMMARY

Consequently, an object to be achieved is to provide an over pressure protection with a cryoprobe for open fluid cooling, where great demands are made on the safety, as well as the efficiency, of the system. Furthermore, equipping a cryoprobe with overpressure protection should be economically feasible and should not affect the design size of the instrument.

In accordance with the embodiments of the invention, this object is achieved by an adapter for connecting a supply system to a cryoprobe for open fluid cooling, said adapter comprising: a first fluid adapter connector for connecting a first supply terminal of the supply system; a second fluid adapter connector for connecting a second supply terminal of the supply system; a feed line output for connecting a feed line of the cryoprobe; a first fluid line for the fluid connection between the first fluid adapter connector with the feed line output; and a second fluid line for the fluid connection of the supply output with the second fluid adapter connector, where the fluid flow in the second fluid line is reduced with respect to the fluid flow in the first fluid line.

Consequently, a central idea of the present disclosure is that existing supply connections are used to discharge fluid in the case of excess pressure. In closed systems, a supply system for a cryoprobe can already comprise appropriate safety mechanisms. The adapter in accordance with the embodiments of the invention allows the utilization of these safety mechanisms. To prevent a permanent drainage of the fluid through the second fluid line, the fluid flow in this line must be reduced. This can be accomplished inside the adapter or in the supply system. Due to the novel adapter, a complex, large-design and expensive pressure relief valve in the cryoprobe is unnecessary. The connected cryoprobe is efficiently and reliably secured by the second fluid line.

It is possible to provide at least one restrictor for reducing the fluid flow in the second fluid line. Consequently, the adapter ensures that, in normal mode, no fluid or only an extremely minimal amount of fluid is discharged through the second fluid line. The major portion of the fluid exits through the feed line output into the feed line of the cryoprobe and provides the cooling capacity wanted there. The restrictor may be selected to be device-specific. Alternatively, the restrictor can be adjusted depending on the cryoprobe that is being connected.

The adapter can comprise at least one third fluid connector for closing at least one third supply terminal. The supply systems of German publication DE 10 2006 003 571 A1 and German application number 10 2008 038 310 comprise several supply connections, in particular three, to operate the cryoprobes with front pressure regulation and rear pressure regulation. It is advantageous if the adapter in accordance with the embodiments of the invention closes the supply terminals that are not being used to prevent fluid from exiting at this location. This increases the safety of the user as well as of the patient. Furthermore, any corresponding safety feature within the supply system can be omitted.

At least one of the fluid adapter connectors can be configured to represent a plug connection with the supply system. Consequently, the adapter can be simply and quickly connected to the supply system. A corresponding plug connector can also be provided for the connection of the cryoprobe.

The aforementioned object is also achieved by a cryoprobe with open fluid cooling which comprises an adapter as previously described, as well as a fluid feed line, where the adapter provides an overpressure protection for the fluid feed line.

Consequently, the adapter can be connected with the open cryoprobe or be an integral part of said probe. The cryoprobe can comprise a probe connector for connecting the cryoprobe to the supply system, where the adapter is a component—in particular an integral component—of the probe connector.

To the extent that the adapter comprises the at least one restrictor in the second fluid line, said restrictor may be configured to be specific to the cryoprobe. As a result, a specific value can be set for a specific cryoprobe, at which value the overpressure protection intervenes and discharges the fluid through the second fluid adapter connector.

Furthermore, the object is achieved by a cryosurgical device comprising a supply system for supplying one of the previously described cryoprobes, where the supply system comprises the first and the second fluid connectors.

Consequently, the supply system can be used, to provide a suitable overpressure protection. In particular, existing mechanisms provided for closed systems are utilized. In such a supply system, the second fluid line may terminate in the supply terminal that is usually connected to the return line of closed cryoprobes.

As an alternative or an addition to the at least one restrictor in the adapter, the supply system may also comprise at least one restrictor for reducing the fluid flow through the second supply terminal. Thus, the fluid flow into the second fluid line can be regulated via the supply system.

The at least one restrictor in the supply system can be adjusted to prevent any excess pressure in the cryoprobe. The restrictor should be adjusted depending on the cryoprobe that is being connected.

The supply system can comprise a detecting device for determining the type of connected cryoprobe and a control unit that is in communicative connection with the detecting unit and the restrictor so that the restrictor is adjusted in a type-specific manner.

The cryosurgical device, in particular the supply system, can comprise at least one sensor for determining a fluid flow and/or a pressure through or on the second supply terminal. These sensors can be used to monitor the pressure in the feed line of the cryoprobe. There is no need for another sensor device inside the cryoprobe.

Additional advantageous embodiments are described herein and in the dependent claims.

BRIEF DESCRIPTION OF THE DRAWINGS

Hereinafter, exemplary embodiments of the invention will be described in greater detail with reference to the drawings, in which:

FIG. 3 illustrates a second embodiment of the adapter in accordance with the invention with the supply system.

DETAILED DESCRIPTION

In the description hereinafter, the same reference signs are used for parts that are the same and for parts that have the same function.

Figure 1:
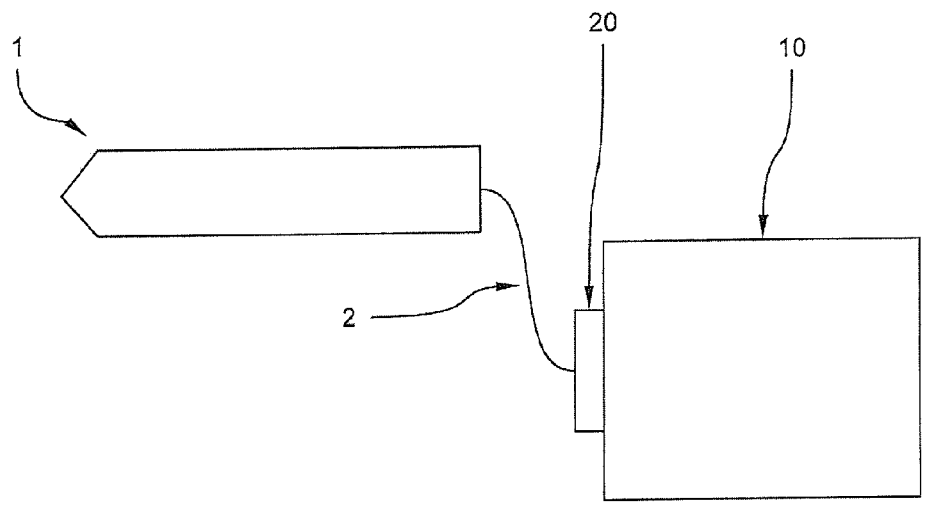
FIG. 1 illustrates a cryosurgical device with an open cryoprobe and a connected supply system.

FIG. 1 shows a cryosurgical device in accordance with an embodiment of the invention, said device comprising a supply system 10 and a cryoprobe 1. A plug connector of the cryoprobe 1 contains an adapter 20 for connecting a cryoprobe feed line 2 of the cryoprobe 1 to the supply system 10. The cryoprobe 1 is an open cryoprobe 1 that has only the cryoprobe feed line 2. A return line is not provided inside the cryoprobe 1. The fluid made available by the supply system 10 is normally not returned into the supply system 10, but is returned to the environment following the expansion of said fluid. The supply system 10 is disposed to operate additional cryoprobes such as for example, those with rear pressure regulation. Furthermore, closed cryoprobes with front pressure regulation can be operated on the supply system 10.

Figure 2:
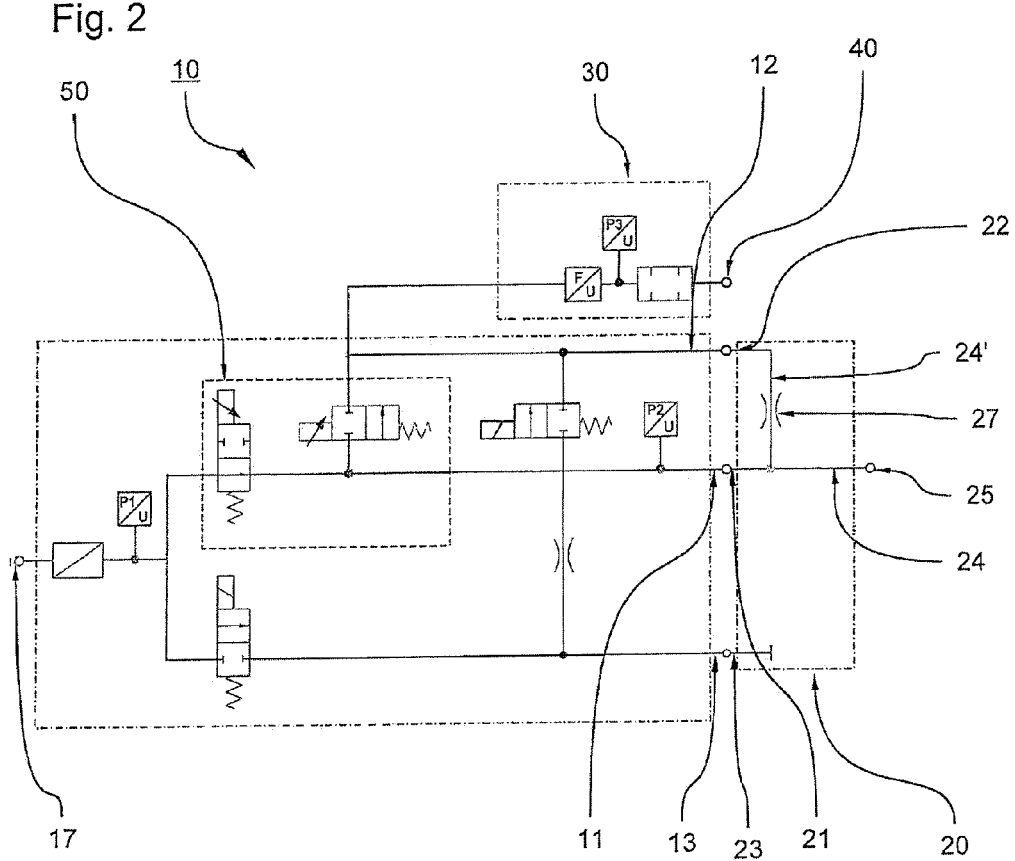
FIG. 2 illustrates a first embodiment of the adapter in accordance with the invention with the supply system.

FIG. 2 shows the adapter 20 and a section of the supply system 10 in detail. As described in greater detail in German patent application number 10 2008 038 310, the supply system 10 can be operated in two modes that are different from each other. In a first operating mode, the cooling capacity of the cryoprobe 1 is adjusted via a front pressure regulation, i.e., by adjusting the pressure in the cryoprobe feed line 2. In the second operating mode, the cooling capacity is adjusted via the return line, i.e., via a rear pressure regulation.

In the first mode, it is possible to operate open and closed cryoprobes. According to the embodiment of the invention, the adapter 20 is provided for operating the open cryoprobe 1. In said first mode, the fluid that is present in pressurized form in a fluid source 17 is conveyed, via a proportional valve unit 50 comprising at least one proportional valve, to a first supply terminal 11. This first supply terminal 11 is in fluid connection with a first adapter connector 21 of the adapter 20. The fluid is transported from the first adapter connector 21 through an adapter fluid line 24 to a feed line output 25 that terminates in the cryoprobe feed line 2. The fluid is expanded inside the cryoprobe 1, preferably near the tip, cools the cryoprobe 1 and is discharged to the environment. Inside the adapter 20 exists a fluid connection between the feed line output 25 and a second adapter connector 22 in the form of an overpressure line 24'. The second adapter connector 22 is in fluid connection with a second supply terminal 12 that is connected to a ventilation unit 40. The overpressure line 24' comprises an adapter restrictor 27 that reduces the fluid flow through the overpressure line 24' such that, in normal mode, only a minimal amount of fluid is discharged through the second adapter connector 22. However, should an overpressure occur in the cryoprobe feed line 2, the fluid is safely discharged through the adapter restrictor 27 to the second adapter connector 22 and then to the ventilation unit 40. The adapter restrictor 27 is adjusted specific to the cryoprobe such that any damage of the cryoprobe 1 or any injury of the patient or the user is prevented. In accordance with the embodiment of the invention, it is possible to provide additional adapters 20 to operate other cryoprobes 1.

Furthermore, the supply system 10 comprises a third supply terminal 13 that, for example, can be used for the connection of cryoprobes that are operated in the second mode. The inventive adapter 20 is in fluid connection with this third supply terminal 13. To do so, said adapter comprises the third adapter connector 23 that closes the third supply terminal 13.

The supply system 10 comprises an optional flow sensor 30 that is in fluid connection with the second supply terminal 12 such that the flow rate on the second supply terminal 12 and/or the pressure existing there can be measured. It is thus possible to detect and indicate an overpressure situation in a timely manner. Furthermore, the supply system 10 can take counter-measures to reduce the occurring pressure. For example, the proportional valve unit 50 can be adjusted such that less fluid at a lower pressure enters the cryoprobe 1.

Considering another exemplary embodiment (cf. FIG. 3), the supply system 10 comprises a supply system restrictor 15. This restrictor is arranged directly downstream of the second supply terminal 12 and is in fluid connection with said supply terminal. The fluid entering through the second adapter connector 22 into the supply system 10 must thus drain through the connecting system restrictor 25 to the ventilation unit 40. Consequently, the supply system restrictor 15 can take over the function of the adapter restrictor 27. Thus, it is also possible to provide the inventive adapter 20 without a corresponding adapter restrictor 27, in which case the same effect can be achieved.

As is shown by FIGS. 2 and 3, the supply system 10 can comprise numerous valves and sensors in order to provide a suitable pressure on the individual supply terminals 11, 12, 13, or to ensure a sufficient pressure gradient between the supply terminals 11, 12, 13.

As has already been mentioned above, the supply system 10 can also be used to operate other cryoprobes, e.g., with a return line. In the first operating mode, the feed line is then connected to the first supply terminal 11 and the return line is connected to the second supply terminal 12. In the second operating mode, the feed line is connected to the third supply terminal 13, and the pressure-stable return line is connected to the first supply terminal 11. Consequently, it is possible, with the appropriate configuration of the supply system 10, to regulate or control the pressure in the return line using the proportional valve unit 50. In each case, the returned gas is discharged through the ventilation unit 40. It is readily apparent that, because of the adapter 20, the individual components of the supply system 10 can be used such that it is also possible to efficiently operate a cryoprobe 1 without return line on said supply system. Additional structural components are not necessary. Consequently, costs can be saved in the manufacture of the supply system 10 as well as in the cryoprobe 1.

The invention claimed is:

1. An adapter for connecting a supply system with a cryoprobe for open fluid cooling, said adapter comprising:
    a first fluid adapter connector for connecting a first supply terminal of the supply system;
    a second fluid adapter connector for connecting a second supply terminal of the supply system;
    a feed line output for connecting a feed line of the cryoprobe;
    a first fluid line for the fluid connection of the first fluid adapter connector with the feed line output; and
    a second fluid line for the fluid connection of the feed line output with the second fluid adapter connector, the second fluid line being configured to receive fluid from the first fluid line as a safety mechanism against overpressure.

2. The adapter of claim 1, further comprising at least one restrictor for reducing a fluid flow in the second fluid line.

3. The adapter of claim 1, further comprising at least one third fluid connector for closing at least one third supply terminal of the supply system.

4. The adapter of claim 1, wherein at least one of the fluid adapter connectors is configured to form a plug connection with the supply system.

5. A cryoprobe with open fluid cooling, comprising:
    an adapter in accordance with claim 1; and
    a fluid feed line,
    wherein the adapter provides an overpressure safety for the fluid feed line.

6. The cryoprobe of claim 5, further comprising a probe connector for connecting the cryoprobe to the supply system, where the adapter is a component of the probe connector.

7. The cryoprobe if claim 6, wherein the adapter is an integral component of the probe connector.

8. A cryosurgical device, comprising:
    a supply system for supplying a cryoprobe as in claim 5,
    wherein the supply system comprises the first and the second fluid connectors.

9. The cryosurgical device of claim 8, wherein the supply system comprises at least one restrictor for reducing a fluid flow through the second supply terminal.

10. The cryosurgical device of claim 9, wherein the at least one restrictor can be adjusted to prevent overpressure in the cryoprobe.

11. The cryosurgical device of claim 10, wherein the supply system comprises a detecting unit for determining the type of the connected cryoprobe and a control unit that is in communicative connection with the detecting unit and the restrictor to adjust the restrictor in a type-specific manner.

12. The cryosurgical device of claim 8, further comprising at least one sensor for determining at least one fluid flow and/or a pressure through or on the second supply connector.

13. The cryosurgical device of claim 8, further comprising a third supply connector for connecting a rear pressure regulation cryoprobe.

14. The adapter of claim 1, wherein a fluid flow in the second fluid line is reduced compared with a fluid flow in the first fluid line.

* * * * *